United States Patent [19]
Conlon et al.

[11] Patent Number: 6,151,407
[45] Date of Patent: *Nov. 21, 2000

[54] MEASUREMENT SYSTEM

[75] Inventors: Peter Conlon; Sean Michael O'Neill; James Mahon, all of Dublin, Ireland

[73] Assignee: MV Research Limited, Dublin, Ireland

[*] Notice: This patent issued on a continued prosecution application filed under 37 CFR 1.53(d), and is subject to the twenty year patent term provisions of 35 U.S.C. 154(a)(2).

[21] Appl. No.: 08/904,625

[22] Filed: Aug. 1, 1997

[30] Foreign Application Priority Data

Aug. 2, 1996 [IE] Ireland ........................... 960563

[51] Int. Cl.⁷ ........................................... G06K 9/00
[52] U.S. Cl. ..................... 382/153; 382/147; 901/47; 362/294
[58] Field of Search ..................... 382/153, 146, 382/148, 145, 147, 149, 151, 152, 144; 313/45, 46; 362/249, 250, 251, 800, 294, 373; 901/47, 35; 348/87, 88, 125, 126, 131, 132

[56] References Cited

U.S. PATENT DOCUMENTS

| | | |
|---|---|---|
| 4,794,647 | 12/1988 | Forgues et al. ........................ 382/147 |
| 4,858,089 | 8/1989 | Pietro ........................................ 362/294 |
| 4,983,887 | 1/1991 | Nilssen ..................................... 315/224 |
| 5,027,295 | 6/1991 | Yotsuya ................................... 382/147 |
| 5,302,836 | 4/1994 | Siu . |
| 5,394,246 | 2/1995 | Sugawara ............................... 356/394 |
| 5,483,603 | 1/1996 | Luke et al. ............................. 382/147 |
| 5,517,235 | 5/1996 | Wasserman ............................ 348/126 |
| 5,552,890 | 9/1996 | Nanna et al. ........................... 356/369 |
| 5,724,439 | 3/1998 | Mizuola et al. ........................ 382/149 |
| 5,757,479 | 5/1998 | Haga et al. ............................. 356/237 |
| 5,784,484 | 7/1998 | Umezawa ................................ 382/148 |

FOREIGN PATENT DOCUMENTS

| | | |
|---|---|---|
| 0 634 892 | 1/1995 | European Pat. Off. . |
| WO91/12489 | 8/1991 | WIPO . |

*Primary Examiner*—Amelia Au
*Assistant Examiner*—Vikkram Bali
*Attorney, Agent, or Firm*—Jacobson, Price, Holman & Stern, PLLC

[57] ABSTRACT

A measurement system (1) has robotic system (3) mounted over a base plate (2) which provides a vertical height reference. In the optical head (8), a CCD camera (17) is adjustable to be pre-set in height. The optical head (8) also has an upper light source (18) comprising LEDs and a lower light source (25) comprising a white fluorescent lamp (26) for lateral component illumination. An air flow system (45) directs cooling air in a swirling motion around the tube. An image analysis computer (10) automatically performs various tests to co-ordinate optical and mechanical operation.

17 Claims, 9 Drawing Sheets

MEASUREMENT SYSTEM

INTRODUCTION

1. Field of the Invention

The invention relates to a measurement system, and more particularly to a system for identifying components on an electronic circuit board and measuring their locations. Such systems generally comprise a support for supporting the circuit board and a robotic system which drives an optical head having a camera connected to an image processor.

2. Prior Art Discussion

EP 634892 (Citizen) describes a system which has a light source comprising a plurality of LEDs and a light shielding arrangement. WO 91/12489 (ABOS) describes a system having a light transmission arrangement which is specific to a particular type of component being measured. While these systems appear to be quite effective for particular applications, they appear to be limited in their range of applications. U.S. Pat. No. 5,302,836 (Siu, B) describes a system which has multiple rings of illumination focused towards their axes. It appears that it would be difficult to control and drive such an arrangement in a high-speed real-time manufacturing environment.

OBJECTS OF THE INVENTION

One object is to improve the "optical chain" signal from the components to the processor to allow accurate and repeatable measurements in a robust system suitable for a manufacturing environment.

Another object is to provide a simpler measurement system, leading to lower cost and simpler maintenance.

SUMMARY OF THE INVENTION

According to the invention, there is provided a measurement system comprising:

a robotic system mounted on a base;

an optical head driven by the robotic system and comprising a light source and a camera;

an image analysis computer connected to the optical head and comprising means for capturing circuit board images and using the images to measure component locations;

characterised in that, the camera is mounted on the optical head in a vertically adjustable manner; and the light source means comprises:

an upper set of light emitting diodes mounted in a ring arrangement for near-on-axis illumination, and means for switching said light emitting diodes, a lower annular fluorescent lamp, and means for cooling air under the fluorescent lamp.

By providing two light sources optimum illumination may be achieved. For example, the LEDs may be switched on for fiducial measurement and off for component measurement. The fluorescent lamp provides comprehensive lateral and diffuse illumination for component measurement. By cooling the air under the lamp, heat shimmer distortion is avoided in a very simple manner and the benefits of a fluorescent lamp may be availed of.

In one embodiment, the fluorescent lamp is of white colour and has a higher intensity than the light emitting diodes. This is particularly effective for component measurement.

Preferably, the light source further comprises a reflector surrounding the fluorescent lamp and its upper side and its outer periphery to provide additional diffuse illumination. This allows the fluorescent lamp provide both direct (mainly lateral) illumination and diffuse illumination arising from reflection.

In one embodiment, the cooling means comprises means for directing cooling air in a swirling motion around the fluorescent tube. This is a simple and effective way of avoiding heat shimmer. The air directing means may comprise air ducts within the reflector and having at least two mutually complementary air outlets. This arrangement is simple as it results in few parts. The outlets are preferably located at approximately the central vertical position of the lamp.

In one embodiment, the fluorescent lamp is operated at a frequency of 23 to 40 kHz. This avoids image intensity "beat", leading to high accuracy and stability.

Preferably, the robotic system comprises means for adjusting vertical position of the optical head. In one embodiment, the optical head comprises means for adjusting vertical position of the fluorescent lamp, and said adjustment means comprises a snap-fitting connector. These arrangements allow versatility to the extent of providing for pre-reflow or post-reflow component measurement.

Preferably, the camera has a tele-centric gauging capacity. In one embodiment, the optical head comprises means for rapid switching of the LEDs. This allows fast operation by minimising delay between fiducial and component measurement.

In another embodiment, the image analysis computer comprises a frame grabber with a pixel jitter value of less than 5 ns.

Preferably, the system comprises a support frame having a mass in excess of 1000 kg, and the robotic system base plate is point mounted onto horizontally milled upper surfaces of the frame. This is a very important feature as it ensures stability and level positioning of the robotic system.

In one embodiment, the image analysis computer is programmed to perform repeatability tests comprising the steps of:

for each of a plurality of optical head acceleration values performing a plurality of component measurements and recording time duration and a standard deviation of the measured location;

plotting responses of said standard deviation and time versus acceleration; and determining an optimum optical head acceleration value based on both of said plots analyses in conjunction with each other.

This provides for repeatability and optimum acceleration in a very simple manner In one embodiment, the image analysis computer comprises means for performing automatic scaling by:

directing movement of a reference target to the optical head field of view;

directing robotic movement of the target with an accuracy of less than +/−5.0 microns over the working area and determining the corresponding movement in the image as a number of pixels; and determining a correlating relationship between the robotic and image movements and using said relationship to determine and store a fresh scaling factor.

Preferably, the image analysis computer comprises means for storing in a database a flag indicating components which are larger than the field of view, and for capturing images of pads in rows of such components when they are identified and subsequently merging the associated measurements to generate a composite measurement.

In one embodiment, the image analysis computer comprises means for directing a second pass for components which are identified in a database as potentially having different identification colours, the second pass being initiated according to comparisons with grey scale thresholds on the first pass and being limited to a pre-defined area of the component.

In a further embodiment, the computer performs initial view allocation, and in a second pass eliminates single-component views of the component in another view, where possible.

Ideally, the computer stores a computer aided design circuit board layout, displays the layout, and adjusts component colours according to measured parameter trends.

In one embodiment, the computer applies a colour-coding scheme to each parameter tracked.

DESCRIPTION OF THE INVENTION

BRIEF DESCRIPTION OF THE DRAWINGS

The invention will be more clearly understood from the following description of some embodiments thereof, given by way of example only with reference to the accompanying drawings, in which.

DETAILED DESCRIPTION OF THE PREFERRED EMBODIMENTS

Referring to the drawings, and initially to FIGS. 1 to 4, there is illustrated a measurement system of the invention indicated generally by the numeral 1. The system 1 comprises a base plate 2 having a machined upper flat surface which provides a base reference for the system. A robotic system 3 is mounted over the base plate 2 on a pair of rails 4 mounted on risers 5, in turn mounted on the base plate 2. The height of the risers is carefully selected as this height provides the base height for the robotic system and the optical head which it drives. In more detail, the robotic system 3 comprises a longitudinal drive 6 and a transverse drive 7, both of the linear motor system type.

Figure 1:
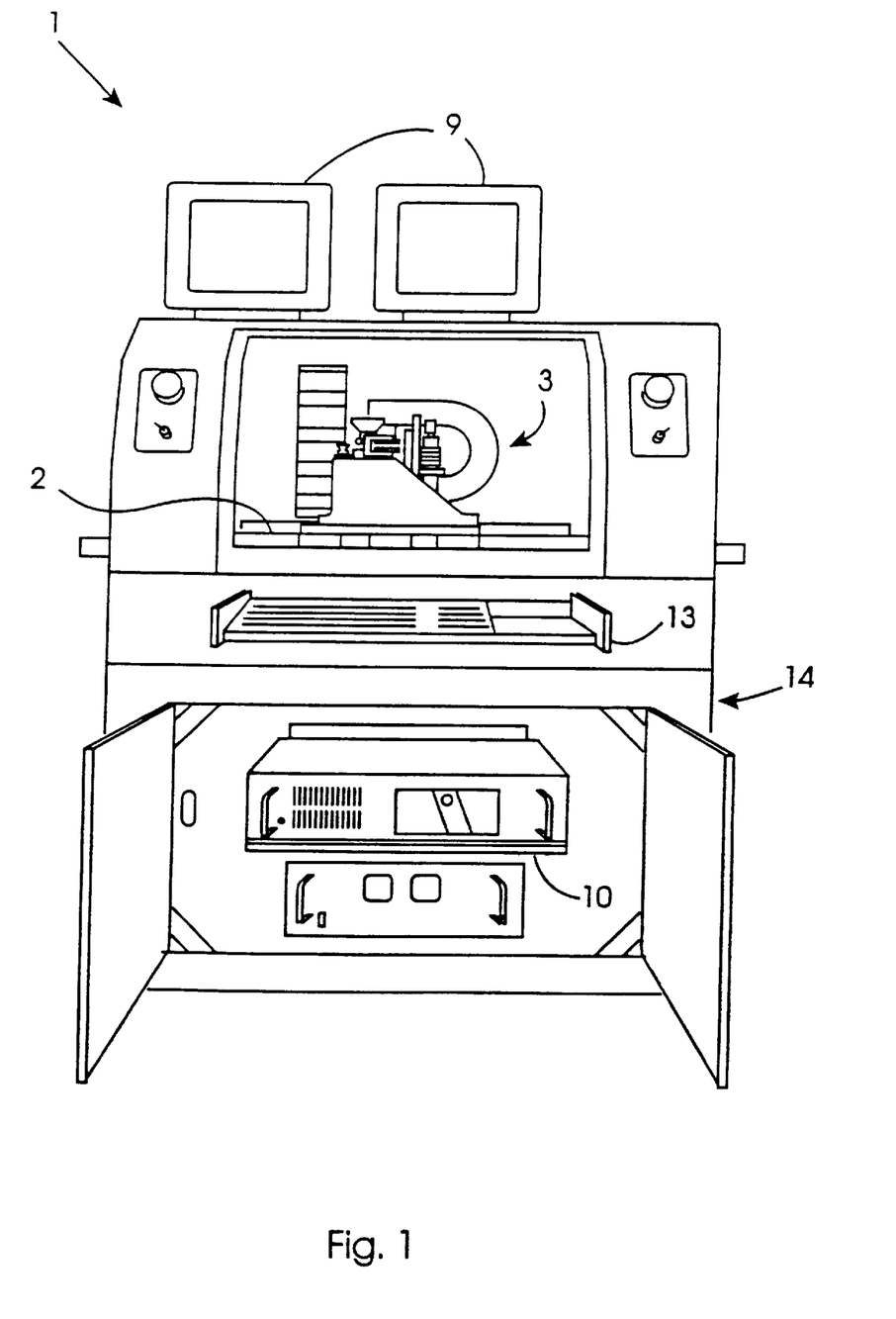
FIG. 1 is a front view of a measurement system of the invention.
Figure 2:
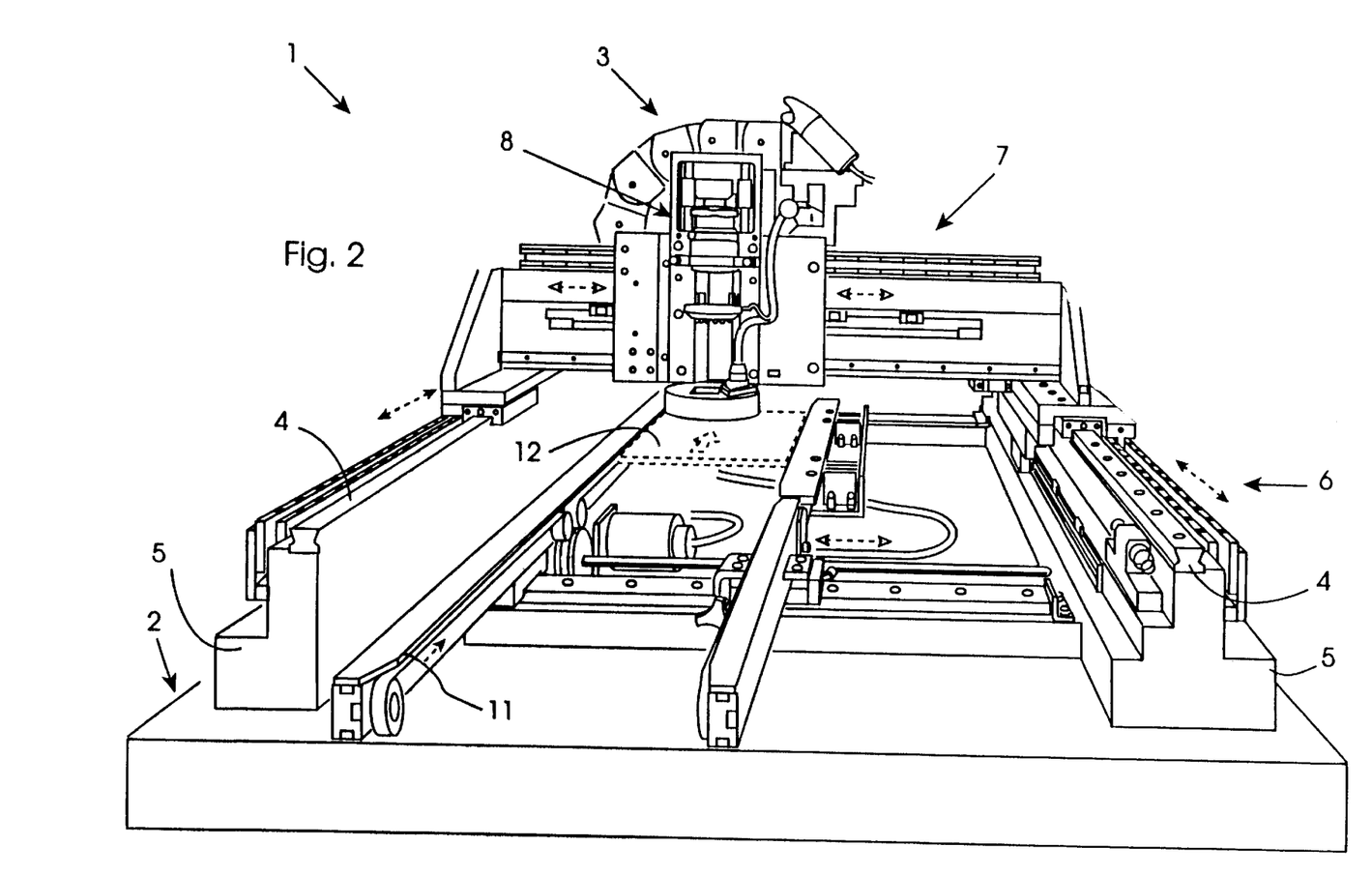
FIG. 2 is a more detailed and side perspective view of the system.
Figure 3:
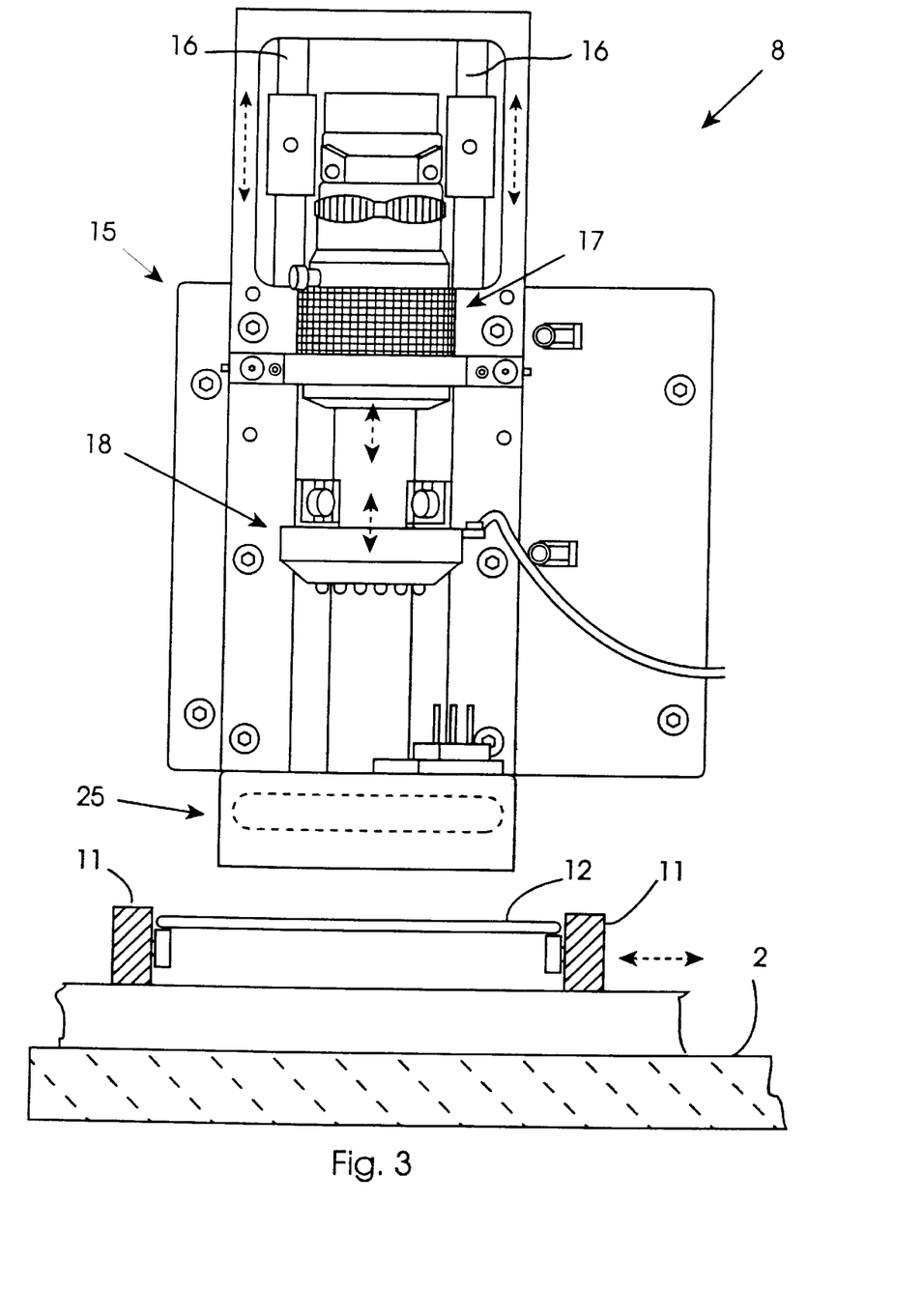
FIG. 3 is a side view showing an optical head of the system.
Figure 4:
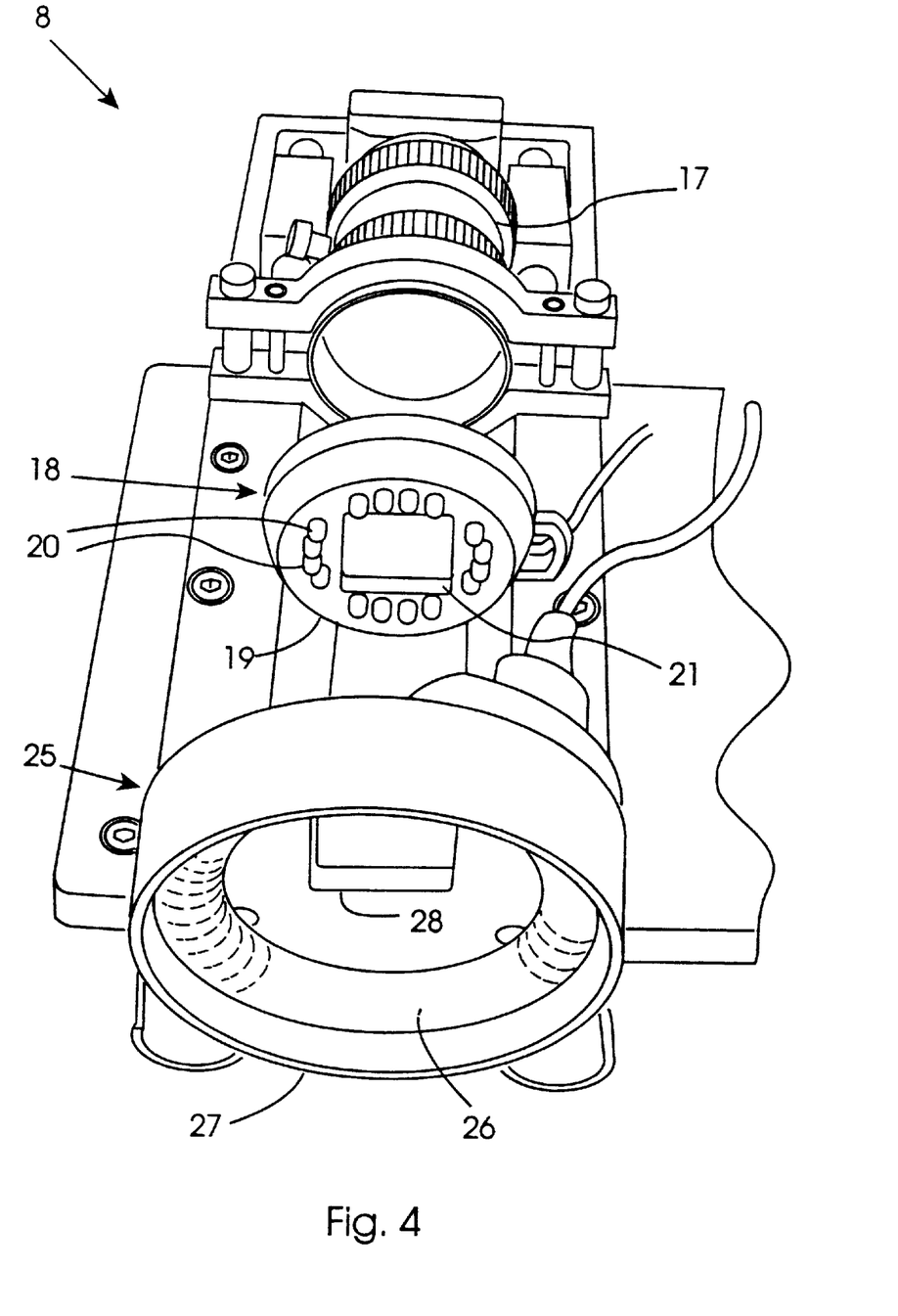
FIG. 4 is a perspective view from underneath of the optical head.

An optical head 8 is mounted on the robotic system and is connected to display screens 9 via an image analysis computer 10. The computer 10 has a frame grabber with a jitter value of less than 5 ns. In addition to performing image analysis, the computer 10 also performs motor control and digital input/output functions. Conveyor rails 11 are mounted above the base plate 2 and beneath the optical head 8 and these are for conveying printed circuit boards (PCB's) 12 underneath the optical head for measurement of components on the board. The apparatus also comprises a keyboard 13 on sliding rails, as shown in FIG. 1.

The base plate 2 is point mounted on a heavy support frame 14 which houses the computer 10. The frame 14 has a mass in excess of 1000 kg, and the plate 2 is bolted at six upper surfaces which have been machined in a single pass to ensure that they are level.

The optical head 8 is mounted on a support block 15 having a pair of vertical bars 16 onto which a camera 17 is mounted. The camera 17 is of the CCD type and has a tele-centric gauging lens. It is mounted on the bars 16 in a manner which allows vertical pre-setting.

The optical head also comprises, beneath the camera 17, an upper light source 18 comprising a support 19 supporting a ring of red light emitting diodes (LEDs) 20 around an aperture 21. The optical head 8 also comprises a lower light source 25 comprising a ring-shaped white fluorescent lamp 26 mounted in a reflective housing 27. The housing 27 has an aperture 28 which is larger than the maximum field of view of the camera 17.

The system 1 is suitable for use before or after reflow in a surface mount technology (SMT) manufacturing process so that trends in the placement operations can be determined from the measurement results. The system 1 initially measures the position of fiducials on the printed circuit (PCB) using the near on-axis illumination of the LEDs 20. The system 1 then measures each component's position relative to the fiducial coordinates and identifies the components. Due to a combination of optical and drive features, the system achieves very high accuracy and excellent repeatability in making measurements at production rates to provide real-time statistical trends of the manufacturing process. This is invaluable to the manufacturer as the trend information allows a preventative maintenance program to be implemented for the placement machines in the process.

Figure 5:
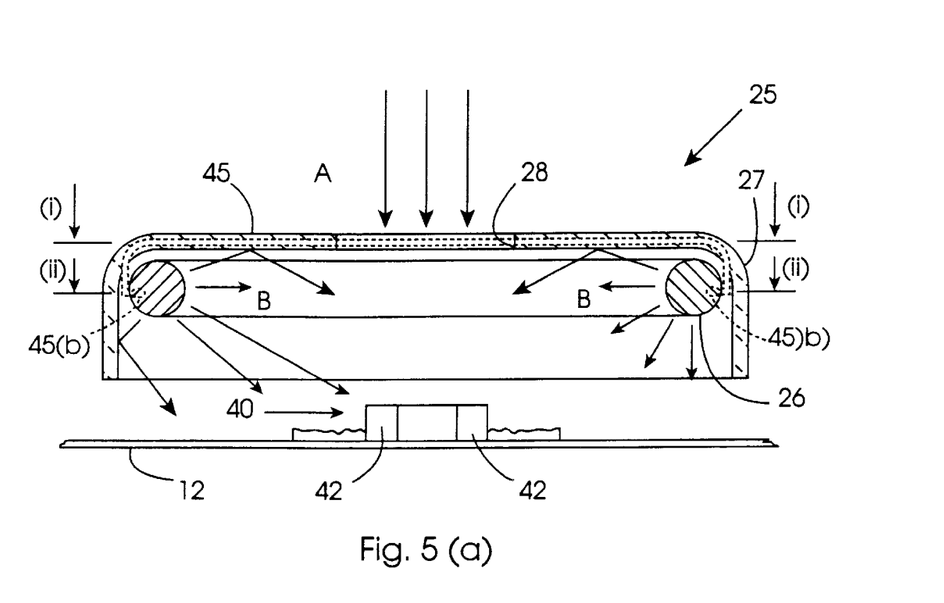
FIG. 5(a) is a diagrammatic cross-sectional front view of a lower light source.
FIG. 5(b) and 5(c) are plan views according to the arrows (i)—(i) and (ii)—(ii) of FIG. 5(a) respectively.

Referring now to FIG. 5, the manner in which a component being measured is illuminated is now described. The upper light source 18 generates a near-on-axis red light beam A directed vertically through the aperture 28. The beam A is relatively weak and is useful primarily for identifying fiducials at the beginning of a measurement process. Thus, the LEDs 20 are rapidly switched for fiducial measurement before component measurement.

As is clear from FIG. 5(a), the fluorescent lamp 26 is close to the level of the PCB, extends in a circle having a larger diameter than the field of view, and is surrounded by a reflective housing which extends downwardly. Because of this arrangement light rays B both impinge laterally on the target and also provide diffuse illumination by reflecting from the reflector surfaces. In this drawing, an SMT component 41 having leads 42 is within the field of view. An important aspect of the lighting arrangement is that the light rays B impinge on the sides of the component 41, namely at the leads 42 and some of them reflect upwardly within the field of view to be captured by the camera 17. This puts a large degree of emphasis on the sides of the components, and more particularly the leads 42. As these are the most important parts of the components for measurement purposes, this optical emphasis reduces the complexity of image analysis which is required and therefore allows a faster response time for real-time measurement to be achieved. Because white light is emitted by the lamp 26, the computer 10 may capture and display colour or monochrome images for analysis. Another important aspect of the lower light source 25 is that high-frequency (the frequency level being 23–40 kHz) fluorescent lighting is used so that image capture "beat" is avoided. These advantages stem largely from use of a fluorescent lamp. However, such a type of lamp has previously been dismissed as a viable option as it results in heat shimmer distortion. In the invention, this problem has been overcome by use of an air flow system illustrated in FIGS. 5(a), 5(b), and 5(c). As illustrated, an internal duct 45 having an inlet 45(a) at the rear extends forwardly from the inlet, laterally in both directions across the top plate of the housing 27, and then downwardly to outlets 45(b). As is clear from FIG. 5(c), the configuration of the outlets 45(b) is such that the air pumped through the duct 45 exits at the outlets 45(b) and flows with a swirling motion inside the housing 27 and around the lamp 26. For clarity, the lamp is not illustrated in FIG. 5(c). It has been found that the air flow system is a very simple, effective, and inexpensive way preventing heat shimmer. It thus allows use of a fluorescent lamp so that the system can avail of the advantages of high frequency, high intensity, and low lamp cost.

Referring again to FIGS. 1 to 4 the optical axis of the system is configured so that it is parallel to the z vertical axis of the robotic system 3, but offset in one direction by a pre-determined amount. Further, the risers 5 are of a specific height to ensure that the focal plane of the camera 17 is centred around the point of inspection. As shown most clearly in FIG. 3, the optical head 8 is mounted onto the support block 15 by bolts. Thus, the vertical position of the optical head can be adjusted by removing the bolts and re-inserting them in different tapped holes with the head 8 at a higher level. This simple adjustment allows use of the system for post-reflow component measurement. For such measurement, the head is adjusted to a higher level, and so the light beams are at a larger angle to horizontal. At the post-reflow stage, the solder has formed a solidified solder fillet against the component, which reflects such light away, thus causing darkness at the solder image location and therefore improving definition and discrimination.

Height of the lower light source 18 may alternatively by adjusted by connecting the reflector housing 27 to an upstanding carrier which slides relative to the support block. The carrier may be configured for snap-fitting engagement at pre-set positions.

The features allow very flexible use of the system 1. For example, by substituting the optical head with one having a different camera and adjusting height the number of pixels per view can be dramatically increased per improved performance where required.

Figure 6:
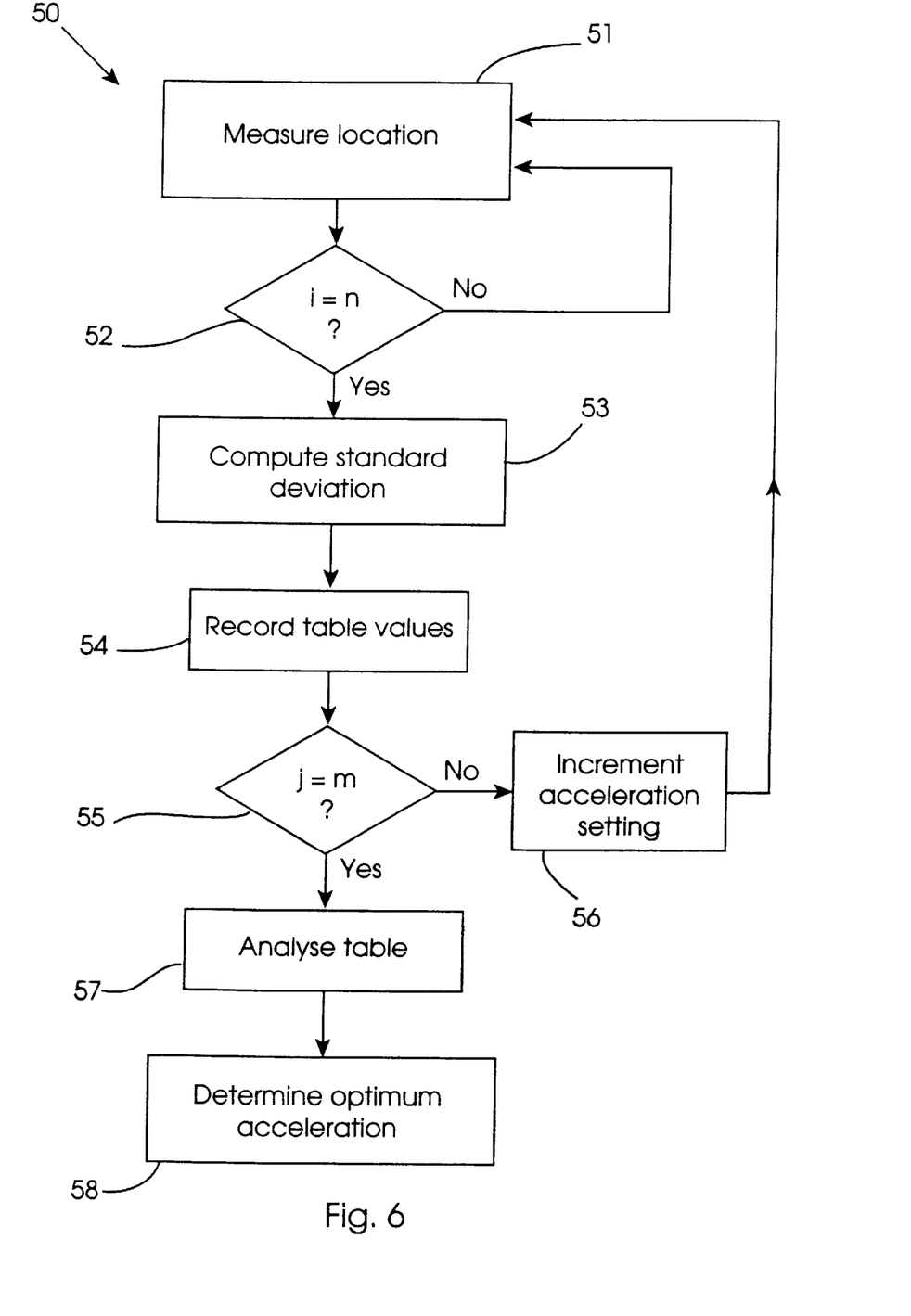
FIG. 6 is a flow diagram illustrating the manner in which the system performs automated repeatability tests.

Another aspect of the manner in which optical and mechanical drive features are combined to achieve high accuracy and excellent repeatability is the fact that the system 1 carries out repeatability tests, as described in the flow diagram of FIG. 6. In this drawing, a method 50 is illustrated which has the initial step 51 of measuring the location of a particular target on the X and Y axes and monitoring the time taken to make the measurement. As indicated by the decision step 52, step 51 is repeated n (in this case, 3) times, after which in step 53 the computer 10 computes X and Y standard deviations XRR and YRR and an aggregate measurement time. In step 54, the computer 10 stores a value for the standard deviation for the particular robotic system optical head acceleration values, and also stores the value for the aggregate measuring time for the acceleration values. The following is an example of a table which is stored.

Acceleration
($\mu$m/ms$^2$)

| X | Y | n | Time(ms) | XRR | YRR |
|---|---|---|----------|-----|-----|
| 2.0 | 1.0 | 3 | 280 | 6 | 7 |
| 3.0 | 1.5 | 3 | 230 | 6 | 8 |
| 4.0 | 2.0 | 3 | 215 | 8 | 9 |
| 5.0 | 2.5 | 3 | 205 | 9 | 10 |
| 6.0 | 3.0 | 3 | 200 | 11 | 15 |

Figure 7:
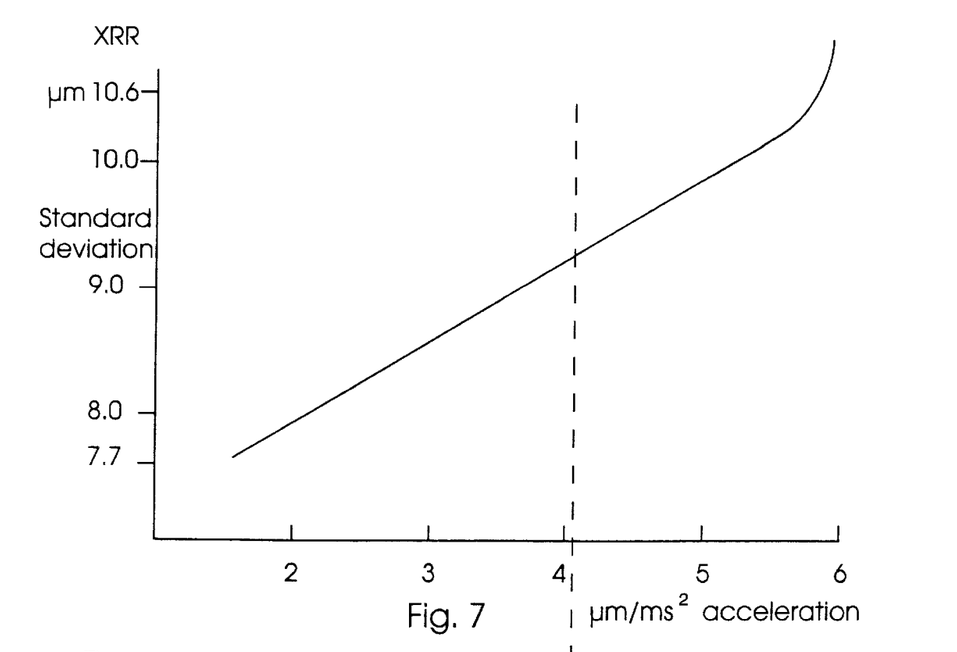
FIGS. 7 and 8 are diagrams illustrating operation of the system to perform automated repeatability tests.
Figure 8:
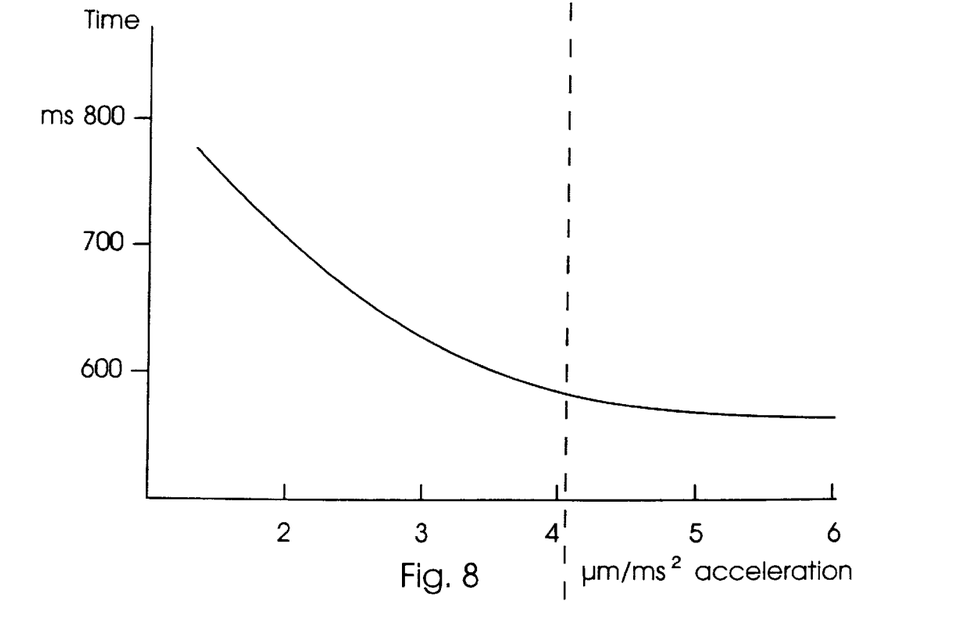

As indicated by the steps 55 and 56, these tests are repeated m times and after each test the computer adjusts the motor control settings to increase the acceleration to a new, incremented value before the next test is carried out. After steps 51 to 54 have been carried out m (in this case, 5) times, tables of values corresponding to the graphs shown in FIGS. 7 and 8 are developed. The former graph plots a vertical axis parameter being six times the standard deviation for the measured location against acceleration on the horizontal axis. It is desirable to use an acceleration which gives the best combination of low RR values and time. In the latter diagram, there is a gradual reduction in the measurement time until an acceleration level of approximately 4 $\mu$m/ms$^2$ is reached. The interrupted line between the two graphs indicates a possible optimum acceleration level to achieve a narrow standard deviation with a low measurement tome for optimum results. This acceleration level is determined in steps 57 and 58 by the computer 10.

Figure 9:
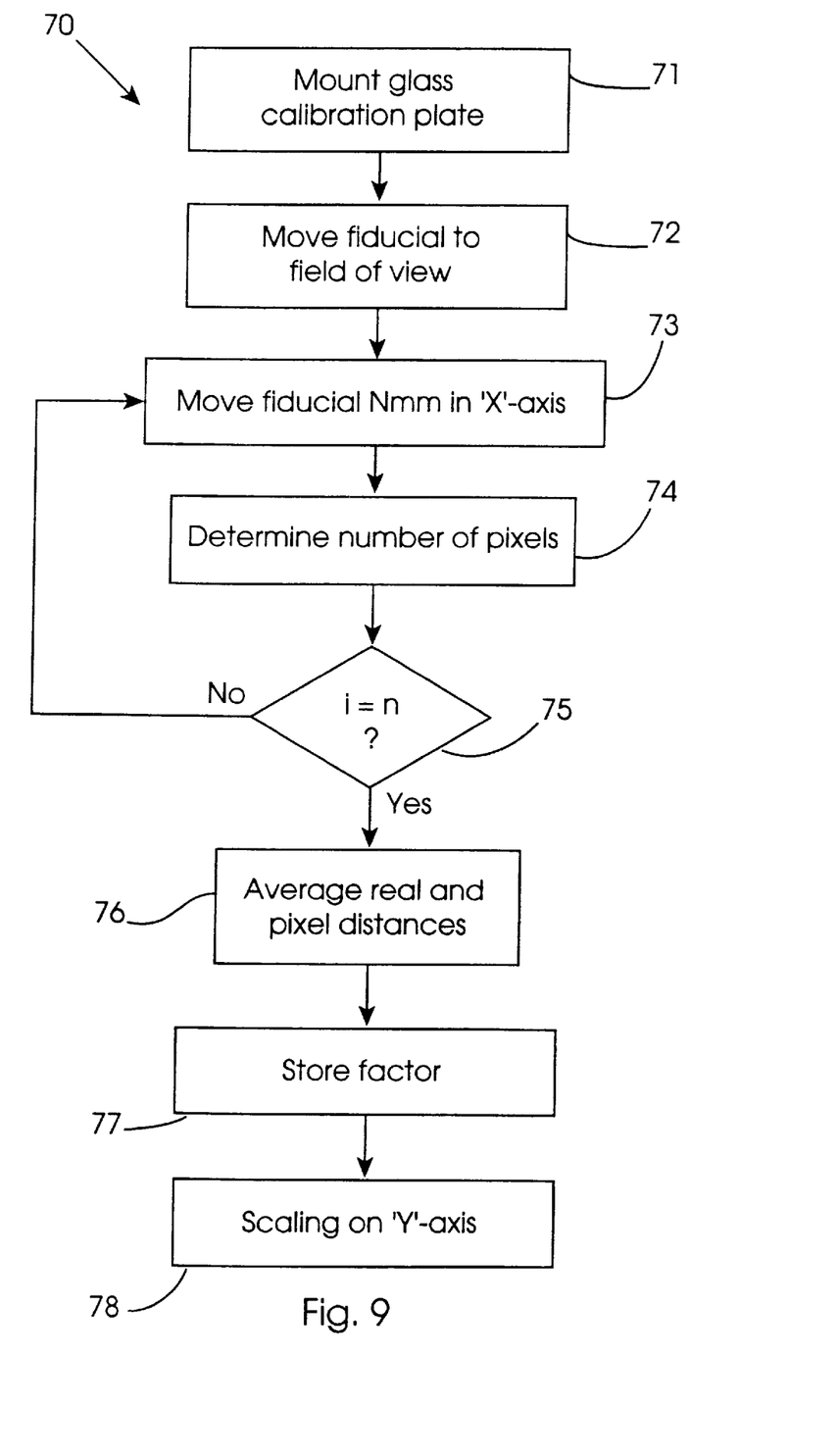
FIG. 9 is a flow diagram illustrating the manner in which the system performs automatic scaling.

The system 1 also combines optical and mechanical drive features in an automatic scaling process 70 shown in FIG. 9. In this process, in step 71 a glass calibration plate is mounted beneath the optical head 8 and in step 72, the robotic system 3 moves the plate to cause a precision fiducial reference mark on the plate to be located within the field of view. In step 73, the robotic system 3 moves the fiducial a total of Nmm with an accuracy of +/−5.0×10$^{-6}$ m over the working area on the X axis. This level of mechanical drive accuracy is achieved by use of a linear motor drive system and accurate machining of the base plate, risers and rails. In step 74, the computer 10 determines the number of image pixels ("pixel distance") which the fiducial mark traverses during this physical motion, using sub-pixel measurement algorithms. As indicated by the decision step 55, the steps 73 and 74 are repeated n times and in step 76 the physical distances of the robotic system and the "pixel distances" are averaged. In step 77, the computer 10 stores an automatic scaling factor correlating these two distances. Then, as indicated generally by the steps 78, it repeats steps similar to steps 71 to 77 for the Y axis. This automatic scaling is achieved because the robotic system employed is accurate to one micron repeatability and +/−5.0 micron accuracy over the working area and use of highly accurate sub-pixel algorithms in conjunction with the optimum lighting head configuration.

Figure 10:
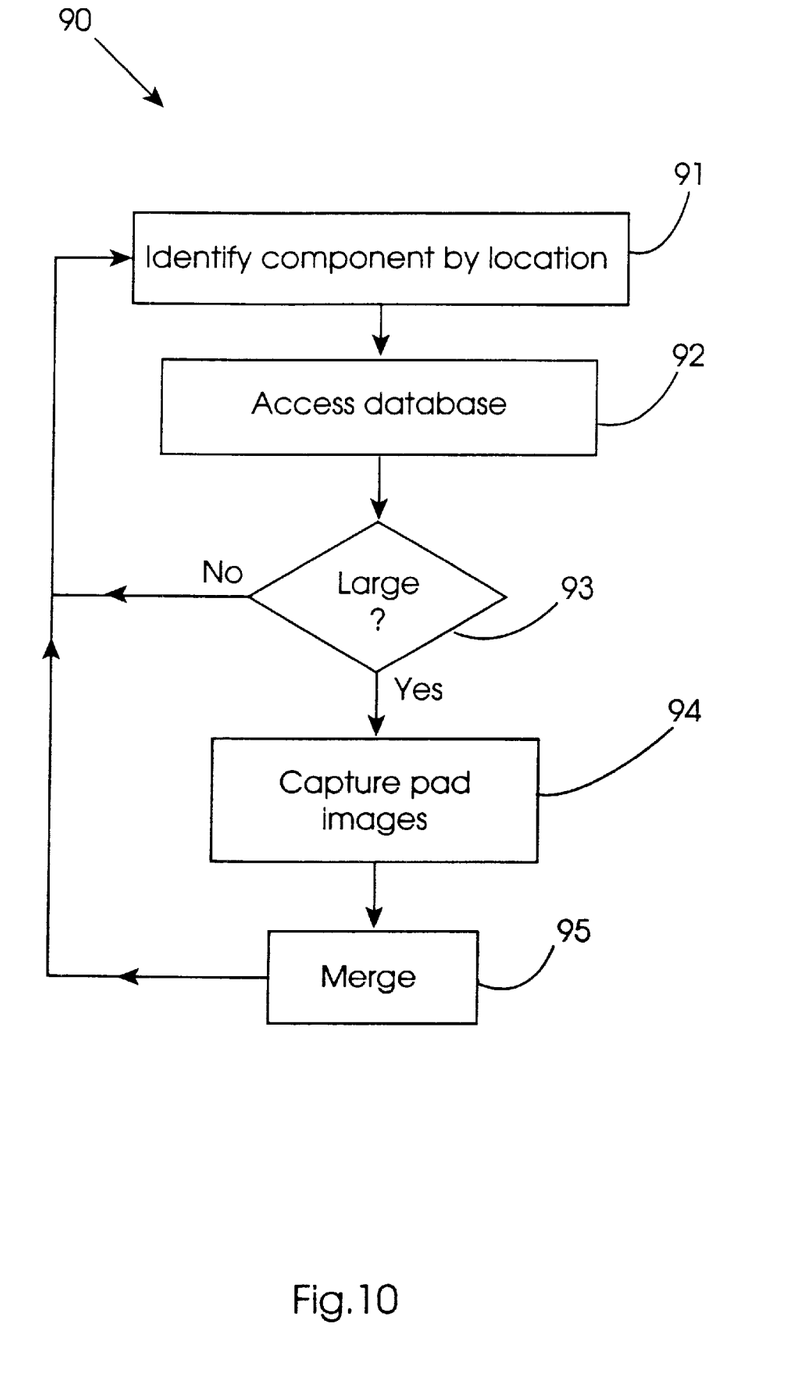
FIG. 10 is a flow diagram illustrating the manner in which the system monitors large components.

The manner in which the system 1 deals with components which are larger than the field of view is illustrated by the process 90 in FIG. 10. In this process, in step 91 the computer 10 recognises a component by virtue of its measured location and by cross-reference to a database indicating such large components by a data record flag. These latter steps are indicated by the step 92 and as indicated by the decision step 93 are repeated for each component identified. Where a large component is identified, in step 94 the computer breaks the component into four sub-components or "row" of pads and then inspects each row in isolation. A row naming scheme is used by the computer 10. For example, the component may be called u200 and the system would break it into four rows of pads, one from each side. The component is now named u500ne12, u200en10, u200sw12 and u200ws10. Each of these rows of pads is measured in isolation and the results are then merged back together to yield a measurement for the whole component. An important aspect of this process is the fact that the step 94 of capturing the pad images involves tracking of offsets for each measurement, the offset levels being stored in the database. Once the offsets have been correctly retrieved by the computer 10, it is a relatively simple operation to merge the measurements. Thus, while the process 90 may at first appear complex, it may be carried out in real-time with a fast response time.

Another aspect of operation of the system 1 is that the computer 10 differentiates tantalum capacitor components, the colour of which may change without notification. This is achieved by using two grey scale thresholds, a high one for the yellow examples and a low one for the black examples. If the image is above the high threshold, a full measurement result set is generated. If it fails the high threshold test, the central area only is tested against the low threshold and if it is below this, the component is considered to be present, but no X and Y information is generated. This effectively means that multiple image analysis algorithms are employed to cater for a situation where there are two potential solutions.

In controlling the fields of view, the computer performs initial view allocation in which the components are sorted in top to bottom and left to right order. Starting at the top left, a view is "hung" on the first components, and all components that fit within the view are allocated to it in a non-optimal fashion. These components are flagged as unavailable. The search continues with the next component, "hanging" another view and allocating as many components to it as possible and continuing until all of the views are allocated. To eliminate anomalous results arising from single components allocated to views, the computer 10 uses a compactor algorithm in the second pass. This looks at all single component views and checks if the component lies within another view. If it does, it is allocated to that view and the initial view is deleted. In this way, about 5% of the views can be deleted with a corresponding improvment in performance.

For display of captured images, the computer 10 generates a graphical display for ease of viewing of measurement information on a production line. This caters for the fact that there may be as many as 2000 X and 2000 Y measurement data sets for each pcb 12 being measured. The system computes mean X and Y offsets from nominal position and standard deviation of X and Y offsets for each component. Using the mean and standard deviation, and also using known process widths, the system calculates Cp (potential process capability index), K (correction factor), and CpK (process capability index) for each component in real-time. CAD data for the circuit board layout which was previously stored in employed to display a map of the board. By selecting one parameter, the CAD layout map for the circuit board is colour-coded so that the characteristics of individual components become explicit. There is one colour code for each parameter. This display technique gives the operator instant feedback on the manufacturing process.

The invention is not limited to the embodiments hereinbefore described, but may be varied in construction and detail. For example, the air flow system may comprise external tubes connected to the reflector housing. It is not essential that a telecentric gauging lens be used.

What is claimed is:

1. A measurement system comprising:

a robotic system mounted on a base;

an optical head driven by said robotic system and having a light source means and a camera;

an image analysis computer connected to the optical head and having means for capturing circuit board images and, said image analysis computer using the images to measure component locations;

said camera being mounted on said optical head in a vertically adjustable manner;

said light source means including an upper set of light emitting diodes mounted in a ring arrangement for near-on-axis illumination, and means for switching said light emitting diodes;

a lower annular light source; said image analysis computer including a frame grabber with a jitter value of less than 5 ns;

means for performing automated repeatability tests, said means for performing, for each of a plurality of optical head acceleration values, a plurality of component measurements including recording time duration and a standard deviation of the measured component location;

means for plotting responses of said standard deviation and time versus acceleration;

means for determining an optimum optical head acceleration value based on both of said plotting responses analyzed in conjunction with each other;

means for performing automatic scaling by directing movement of a reference target to an optical field of view;

means for directing robotic movement of a target within accuracy of less then +/−5.0 microns over a working area;

means for determining a corresponding movement in an image as a number of pixels;

means for determining a correlating relationship between the robotic and image movements;

means for using said correlating relationship to determine and store a fresh scaling factor;

means for, in real time, recognizing a component larger than the field of view by its measured location and by reference to a database indicating such components by a data record flag;

means for directing capture of an image for each of a plurality of rows of pads;

means for storing an offset for each image in a database;

means for performing measurements for each row of pads in isolation;

means for retrieving the stored offsets;

means for combining the measurements to yield a measurement for the whole component; and means for directing a second pass for components which are identified in a database as potentially having different identification colors, the second pass being initiated according to comparisons with grey scale thresholds on the first pass and being limited to a pre-defined area of the component.

2. The measurement system as claimed in claim 1, wherein the lower annular light source comprise a fluoresent lamp which is of white colour and has a higher intensity that the light emitting diodes.

3. A measurement system as claimed in claim 2, wherein the reflector surrounds the fluorescent lamp at its upper side and its outer periphery.

4. The measurement system as claimed in claim 3, wherein the cooling means comprises means for directing cooling air in a swirling motion around the fluorescent tube.

5. The measurement system as claimed in claim 4, wherein said air directing means comprises air ducts within the reflector and having at least two mutually complementary air outlets.

6. The measurement system as claimed in claim 5, wherein said air outlets are located at approximately the central vertical position of the fluorescent lamp.

7. The measurement system as claimed in claim 2, wherein the fluorescent lamp is operated at a frequency of 23 to 40 kHz.

8. The measurement system as claimed in claim 1, wherein the robotic system comprises means for adjusting vertical position of the optical head.

9. The measurement system as claimed in claim 2, wherein the optical head comprises means for adjusting vertical position of the fluorescent lamp.

10. The measurement system as claimed in claim 9, wherein said adjustment means comprises a snap-fitting connector.

11. The measurement system as claimed in claim 1, wherein the camera has a tele-centric gauging capacity.

12. The measurement system as claimed in claim 1, wherein the optical head comprises means for rapid switching of the LEDs.

13. The measurement system as claimed in claim 1, wherein the system comprises a support frame having a mass in excess of 1000 kg, and a robotic system base plate is point mounted onto horizontally milled upper surfaces of the frame.

14. The measurement system as claimed in claim 1, wherein the computer comprises means for performing initial view allocation and for eliminating single-component views of the component in another view in a second pass.

15. The measurement system as claimed in claim 1, wherein the computer comprises means for storing a computer aided design circuit board layout, for displaying the layout, and for adjusting component colours according to measured parameter trends.

16. The measurement system as claimed in claim 15, wherein the computer comprises means for applying a colour coding scheme to each parameter for which a trend is measured.

17. A measure system as claimed in claim 1, wherein said system further includes:

means for switching the light emitting diodes;

an annular fluorescent lamp mounted beneath the set of light emitting diodes and around the camera field of view;

a reflector extending above and around the fluorescent lamp and said reflector having an inner reflective surface for reflection of light ot provide downwardly-directed diffuse illumination directly from the lamp and reflected from the inner reflective surface;

an aperture to allow-passage of the near-on-axis for illumination generated by the light emitting diodes;

a duct for flow of cooling air around the lamp; and pumping means for pumping cooling air through the duct in the reflector.

* * * * *